Figure 1:
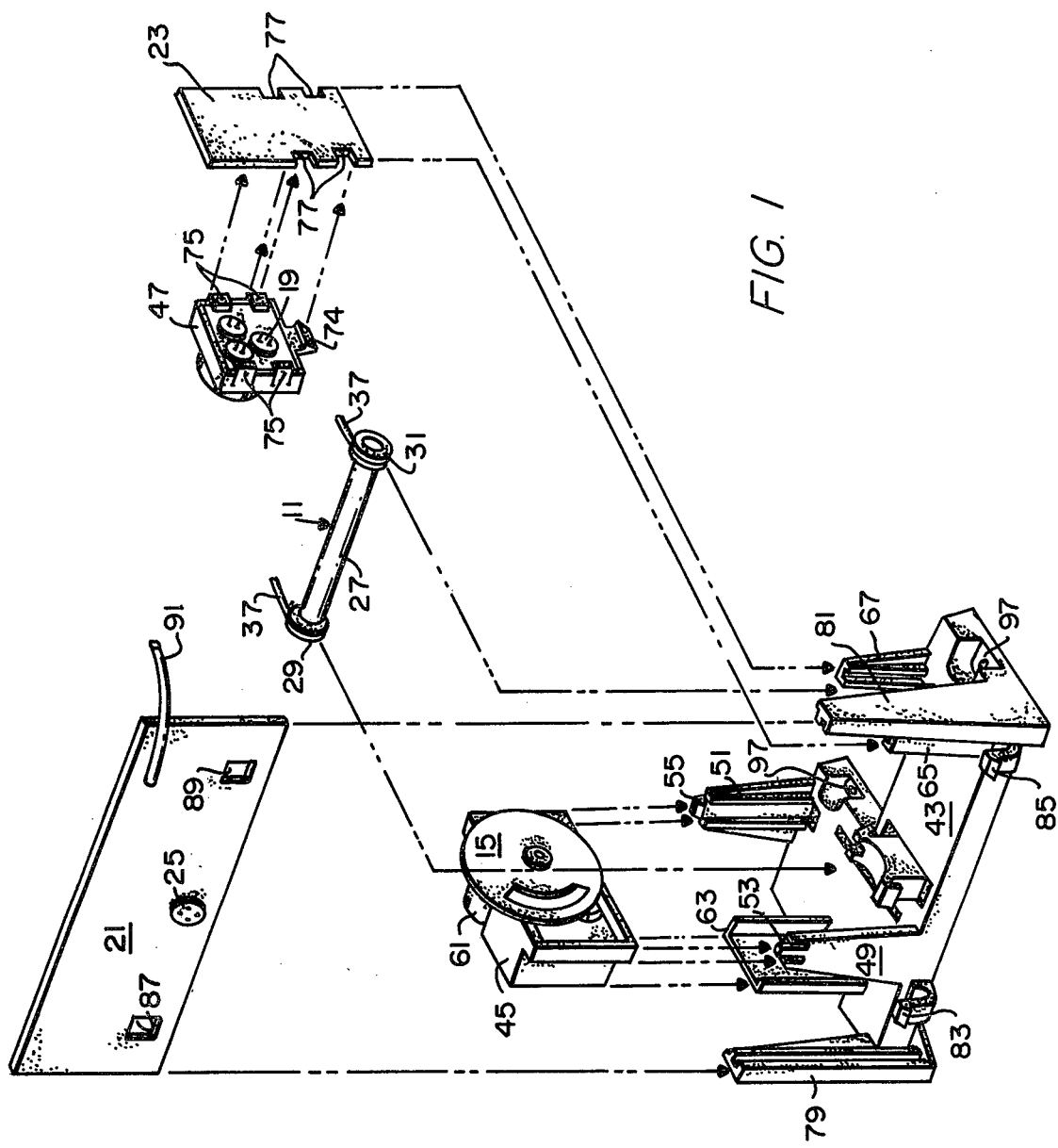

United States Patent [19]

Passaro et al.

[11] 4,437,004
[45] Mar. 13, 1984

[54] MODULAR GAS ANALYZER

[75] Inventors: Robert E. Passaro; Irvin G. Burough, both of Walnut Creek, Calif.

[73] Assignee: Andros Analyzers Incorporated, Oakland, Calif.

[21] Appl. No.: 295,485

[22] Filed: Aug. 24, 1981

[51] Int. Cl.³ .......................... G01J 1/04; G01N 21/01
[52] U.S. Cl. ..................................... 250/343; 356/440
[58] Field of Search ................ 356/246, 440; 250/343, 250/344, 345

[56] References Cited

U.S. PATENT DOCUMENTS

| | | | |
|---|---|---|---|
| 4,013,260 | 3/1977 | McClatchie et al. | 250/343 |
| 4,220,415 | 9/1980 | Staab et al. | 250/343 |
| 4,227,810 | 10/1980 | Sandrock et al. | 356/246 |
| 4,346,296 | 8/1982 | Passaro et al. | 250/343 |
| 4,370,553 | 1/1983 | Waycaster et al. | 250/343 |

FOREIGN PATENT DOCUMENTS 1598535 11/1972 Fed. Rep. of Germany .

*Primary Examiner*—Alfred E. Smith
*Assistant Examiner*—Carolyn E. Fields
*Attorney, Agent, or Firm*—Fitch, Even, Tabin & Flannery

[57] ABSTRACT

An infrared gas analyzer is described wherein infrared energy is directed through a sample cell from a source at one end thereof. A detector at the opposite end of the sample tube monitors infrared energy of at least one pre-selected wavelength in order to produce a signal representative of the infrared energy passing through the sample cell. The analyzer is of modular construction including a disposable sample cell, an infrared source housing, a detector housing and printed circuit boards mounting signal processing components for the analyzer. A mounting base is adapted for receiving the sample tube, housings and printed circuit boards in operating alignment and interconnection with each other, detents positively securing the components in place.

5 Claims, 2 Drawing Figures

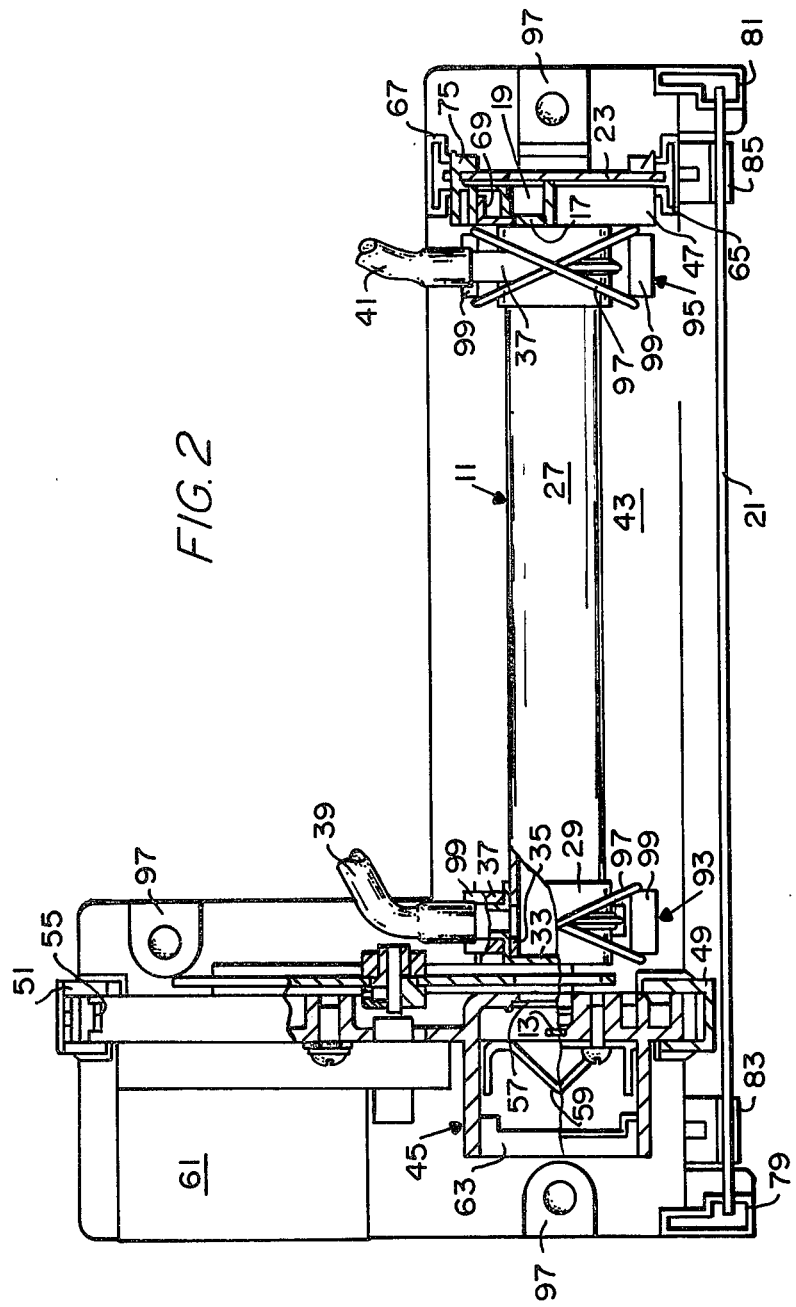

MODULAR GAS ANALYZER

The present invention relates generally to infrared gas analyzers and more particularly to an improved gas analyzer of modular construction being especially adapted for facilitating replacement of a disposable sample cell or tube.

Infrared gas analyzers typically employ an infrared source to produce and direct infrared energy through an unknown gas mixture passed through a sample cell. Energy passing through the sample cell is detected to produce an electrical signal representative thereof. These signals are converted to an output indicating the concentration of one or more of the constituents of the gas in the sample cell. As will be apparent from the following description, such an analyzer may include components and electrical processing channels for detecting one or a plurality of different gases.

Gas analyzers of the type contemplated by the present invention are based on the principle that various gases exhibit substantial absorption characteristics at specific wavelengths in the infrared radiation spectrum. Gas analyzers of this type are shown and described in U.S. Pat. No. 4,013,260 issued to McClatchie et al. on Mar. 22, 1977 and in application Ser. No. 178,302, filed Aug. 15, 1980 by Passaro et al., now U.S. Pat. No. 4,346,296, issued Aug. 24, 1982, both assigned to the assignee of the present invention.

Gas analyzers such as those disclosed in the above references employ a beam of infrared energy passing through the sample cell which contains an unknown gas mixture, the infrared energy beam being varied by the interposition of one or more filters in the path of the beam. Typically, each filter passes only radiation at the characteristic absorption wavelength of a particular gas of interest. One or more additional filters may also be used as reference filters at wavelengths close to but not overlapping the characteristic absorption wavelength for any gas present in the sample cell.

A simplified gas analyzer may also use a stationary filter or multiple filters with associated detectors rather than a rotary filter wheel as described above. Such analyzers cause an AC signal to be produced by the detector by periodically interrupting the infrared beam, for example, with a rotary chopper.

In any event, gas analyzers of the types described above have been relatively complex and expensive in the past while also being relatively difficult to repair because of precise requirements, particularly for the sample cell as well as other components of the analyzer.

It is therefore an object of the invention to provide an improved gas analyzer of simplified modular construction. In this regard, the invention preferably contemplates modular components for an analyzer including a gas sample cell, a source housing, a detector housing, and one or more printed circuit boards, a mounting base for the analyzer including means for receiving and positively and releasable securing the respective components in operating alignment and interconnection with each other.

It is also an object of the invention to provide a gas analyzer including a replaceable and disposable sample cell. In this regard, the invention contemplates an improved infrared gas analyzer having a sample cell of simplified construction including housings at opposite ends of a tubular portion for mounting windows which are substantially transparent to infrared radiation, the housings also including means for respectively communicating gas into and out of the sample cell, the analyzer including means for replaceably securing the sample cell in place between an infrared energy source and a detector means. Accordingly, this feature of the invention facilitates removal and replacement of the sample cell in the analyzer. The sample cell may thus be cleaned and returned to the analyzer if desired. However, the invention particularly contemplates use of a sample cell which is disposable so that it may merely be replaced when necessary in order to facilitate continued operation of the analyzer.

Other objects of the invention will be apparent from the following description, having reference to the accompanying drawings wherein:

FIG. 1 is an exploded view of a modular gas analyzer constructed in accordance with the present invention; and FIG. 2 is a partially schematic view, with parts in section, of an assembly for the gas analyzer of FIG. 1.

Very generally, the infrared gas analyzer of the invention comprises a sample cell 11 for containing the gas mixture to be analyzed. An infrared energy source 13 directs an infrared beam through the sample cell, the beam being periodically interrupted at a predetermined frequency by a chopper wheel 15. The resulting infrared beam passes through the sample cell and one or more filters 17 before encountering a detector 19 associated with each filter. The number of filters and detectors is of course dependent upon the number of gases to be detected or monitored within the sample cell. In any event, an output signal is produced by the detector or detectors representative of infrared energy passing through the sample cell at a preselected wavelength for each gas.

In this regard, operation of the gas analyzer of the present invention is generally conventional at least to the extent that the analyzer includes components which operate for example in the manner disclosed by the Passaro, et al reference listed above. Accordingly, that reference is incorporated herein as though set out in full. In particular, the above noted reference describes a processing circuit for receiving the electrical signal or signals from the detectors 19 and converting them to output signals which are properly representative of the particular gases being monitored within the sample cell.

The processing circuitry for the analyzer is not described in greater detail herein except to note that the circuit components are mounted upon one or more printed circuit boards. For reasons set forth in greater detail below, the circuit components are preferably mounted upon two printed circuit boards 21 and 23. The smaller printed circuit board 23 includes or mounts preamplifier components (otherwise not shown) for each of the gas channels in the analyzer. The larger printed circuit board 21 includes the remaining processor components also not shown) which are thus adapted for receiving one or more amplified signal from the preamplifier section of the printed circuit board 23 in order to produce a suitable output signal. For this purpose, the printed circuit board 21 also includes a connector 25 providing a control interface for the analyzer.

Before describing the modular construction of the analyzer, it is again noted that the sample cell 11 is particularly contemplated as being of disposable construction to readily facilitate its replacement in the analyzer when necessary. For this purpose, the sample cell 11 is formed from an elongated tubular element 27 with similar end caps or housings 29 and 31 adapted for mounting at each end of the tubular element 27. Preferably, the housings 29 and 31 are formed as moulded components adapted for press fit attachment to the tube 27. As may be best seen in FIG. 1, each of the housings 29 and 31 hermetically receives an end closure 33 formed from a material such as mica exhibiting minimum absorption of infrared energy passing through the sample cell. The closure 33 may also be secured within the housings by press fit engagement or by retainers such as that indicated at 35 in FIG. 2. Each of the end housings 29 and 31 also forms a nozzle 37 forming an inlet and outlet for gas passing through the sample cell. For this purpose, the analyzer is illustrated in FIG. 1 with an inlet tube 39 being connected with one of the nozzles and an outlet tube 41 being connected with the other nozzle.

In any event, the construction of the sample cell is very much simplified, the housings 29 and 31 being readily formed for example by moulding, the sample cell this being particularly adapted for disposable use so that it can be readily replaced in the analyzer when it is desired. The manner in which the sample cell is replaceably mounted on the analyzer is described in greater detail below.

Modular construction of the analyzer is facilitated by forming the analyzer in five major sub-assemblies, including a mounting base 43, infrared source housing 45, detector housing 47, the sample tube referred to at 11 and the printed circuit board referred to above at 21. As will be made more apparent below, the smaller printed circuit board 23 forms a portion of the detector housing 47 in order to make the analyzer more compact and to serve a further purpose in connection with the detector housing. The components for each of the modular elements of the analyzer are described below along with the manner in which they are mounted upon the base 43.

Initially, the source housing 45 is adapted to be received by channel members 49 and 51 which extend upwardly from the mounting base and include tangs 53 and 55 at their upper ends for positively securing the source housing in place upon the mounting base. The source 13 is mounted within the housing 45. A transparent window 57, preferably formed from a suitable material such as sapphire, is so mounted in the source housing to permit complete passage of infrared energy from the source into the sample cell. A reflector plate 59 is mounted on the opposite side of the source 13. The source housing 45 is also adapted to receive the rotatable chopper wheel 15 and its drive motor 61. Accordingly, these components may be arranged in place upon the analyzer when the source housing is secured within the channel members 49 and 51. A closure for the end of the source housing opposite the sample cell 11 is preferably provided by a closure element 63 which is formed as an integral portion of the mounting base 43. Thus, when the source housing is mounted in place upon the base 43, its internal components are protected by the closure element 63. At the same time, when the source housing is removed from the base 43, its internal components are immediately accessible due to the open construction of the housing permitted by the closure element 63.

The detector housing 47 is similarly adapted for mounting upon the base 43 by means of channel members 65 and 67 which support the detector housing 47 in spaced apart relation from the source housing 45 to facilitate mounting of the sample cell 11 therebetween. The detector housing 47 includes a filter housing 69 which is preferably mounted within the detector housing by press fit engagement in order to support one or more filters in communication with the sample cell.

A detector 19 is arranged opposite the sample cell from each of the filters 17. As may be best seen in FIG. 1, the detector housing is also of relatively open construction in order to facilitate installation and replacement of internal components. The detector housing has a tang 74 which engages a slot in the base for securing the detector housing in place. Closure of the detector housing is provided by the smaller printed circuit board 23, tangs 75 being formed on the detector housing for engaging slots 77 in the printed circuit board 23 for securing it in place. Mounting of the printed circuit board 23 upon the detector housing also facilitates positioning and interconnection, for example by soldering, of the detectors 19 to the preamplifier components on the printed circuit board 23.

The other printed circuit board 21 including the remaining processor components is also received by channel members 79 and 81 which are arranged upon the mounting base 43 so that the larger printed circuit board 21 extends along one side of the analyzer. The printed circuit board 21 is secured in place upon the mounting base by resilient tangs 83 and 85 which engage slots 87 and 89 on the printed circuit board 21 when it is properly in place upon the mounting base 43. The processing components on the printed circuit board 21 may be interconnected with the preamplifier printed circuit board 23 for example by means of a connector as generally indicated in FIG. 1 at 91. Similarly, the source 13 and chopper motor 61 may be interconnected with respective portions of the control circuit by connectors (not shown).

The mounting base 43 also has saddle brackets 93 and 95 which are respectively adapted to receive the end closures 33 for the sample cell 11. Means for replaceably securing the sample cell in place upon the mounting base preferably include resilient bands 97, in the form of elastomeric 0-rings, which wrap over the housings 29 and 31 and engage projections 99 on the brackets 93 and 95. Mounting brackets 97 are provided on the mounting base 43.

It may thus be seen that the modular construction of the gas analyzer is provided by the present invention particularly facilitates assembly of the various analyzer components upon the mounting base 43. At the same time, the modular construction of the analyzer also facilitates selective removal and/or replacement of various components in the analyzer. In this regard, it is particularly contemplated that the sample cell 11 be of disposable construction in order to facilitate its periodic replacement in the analyzer.

Various modifications of the invention will be readily apparent in addition to those described above. Accordingly, the scope of the present invention is defined only by the following appended claims.

What is claimed is:

1. In an infrared gas analyzer including a sample cell for containing the gas mixture to be analyzed, means for directing infrared energy through said sample cell, source means for periodically interrupting the infrared energy at a predetermined frequency, detector means responsive to infrared energy of at least one preselected wavelength for producing a signal having an amplitude proportional to the infrared energy passing through said sample cell and having a frequency corresponding to the predetermined frequency, said preselected wavelength corresponding to the characteristic absorption wavelength of a preselected gas, and signal processing means for processing the signal output of said detector means to produce a signal representative of the concentration of the preselected gas in the mixture being analyzed, the analyzer being a modular construction to facilitate assembly and replacement of components, comprising a modular sample tube,
   a modular source housing means for mounting the source of infrared energy at one end of said sample tube,
   a modular detector housing means for mounting the detector means at the opposite end of said tube,
   a printed circuit board mounting the signal processing means, and
   a mounting means for supporting said sample tube, source housing means, detector housing means and printed circuit board, said mounting means comprising a unitary structure including a base and a plurality of integral channel members extending transversely from the same side thereof and spaced in pairs to form three substantially parallel pairs of channels for engaging with and locating said source housing means, detector housing means and printed circuit board, respectively, in operative relationship with each other, and detent means for releasably securing said source housing means, detector housing means and printed circuit board in said channel members to enable said source housing means, said detector housing means and said printed circuit board to be readily removed individually for repair or replacement without the need to remove other modular elements.

2. The analyzer of claim 1 wherein said mounting means further including a pair of saddle brackets for mounting said sample tube extending between said source housing means and said detector housing means, and retainer means for releasably securing said sample tube to said saddle brackets whereby said sample tube may be readily removed for disposal.

3. The analyzer of claim 2 wherein said retainer means comprise resilient bands for securing said sample tube to said saddle brackets.

4. The analyzer of claim 1 wherein a portion of said printed circuit board is positioned as a closure on said detector housing means.

5. The analyzer of claim 1 wherein a plate member is formed on said mounting means as a closure for said source housing means.

* * * * *